US007928830B2

(12) United States Patent
Tsubata et al.

(10) Patent No.: US 7,928,830 B2
(45) Date of Patent: Apr. 19, 2011

(54) BIOMETRIC INFORMATION DETECTING APPARATUS

(75) Inventors: Keisuke Tsubata, Chiba (JP); Koichi Moriya, Chiba (JP); Shinichiro Miyahara, Chiba (JP)

(73) Assignee: Seiko Instruments Inc. (JP)

( * ) Notice: Subject to any disclaimer, the term of this patent is extended or adjusted under 35 U.S.C. 154(b) by 1113 days.

(21) Appl. No.: 11/596,515

(22) PCT Filed: Apr. 27, 2005

(86) PCT No.: PCT/JP2005/007990
§ 371 (c)(1),
(2), (4) Date: Jan. 25, 2007

(87) PCT Pub. No.: WO2005/110211
PCT Pub. Date: Nov. 24, 2005

(65) Prior Publication Data
US 2007/0195989 A1    Aug. 23, 2007

(30) Foreign Application Priority Data
May 13, 2004    (JP) .................................. 2004-143592

(51) Int. Cl.
*G06F 7/04* (2006.01)
*H04L 12/28* (2006.01)
*A61B 5/00* (2006.01)
*G06K 9/00* (2006.01)
*G10L 21/00* (2006.01)

(52) U.S. Cl. ...................... 340/5.82; 340/5.81; 340/5.64; 340/5.52; 600/344; 382/100; 382/115; 704/273

(58) Field of Classification Search .................. None
See application file for complete search history.

(56) References Cited

U.S. PATENT DOCUMENTS

| 6,703,918 | B1 * | 3/2004 | Kita | 340/5.52 |
| 6,928,181 | B2 * | 8/2005 | Brooks | 382/115 |
| 7,054,463 | B2 * | 5/2006 | Rhoads et al. | 382/100 |
| 2002/0151775 | A1 * | 10/2002 | Kondo | 600/344 |

* cited by examiner

*Primary Examiner* — Davetta W Goins
*Assistant Examiner* — Fekadeselassie Girma
(74) *Attorney, Agent, or Firm* — Adams & Wilks (57) ABSTRACT

A biometric information detecting apparatus has a biometric sensor for measuring biometric information for a predetermined time period. An A/D conversion portion acquires a sampling data by subjecting an output of the biometric sensor to A/D conversion. A storing portion stores the sampling data. A frequency analyzing portion subjects the sampling data stored in the storing portion to a frequency analysis and stores a result of the frequency analysis to in storing portion. A biometric state value calculating portion calculates a biometric state value from the result of the frequency analysis stored in the storing portion. An SN ratio calculating portion calculates an SN ratio from the result of the frequency analysis stored in the storing portion. A determining portion determines a reliability of the biometric state value based on whether the calculated SN ratio exceeds a predetermined threshold. A measured data storing portion associates a result of the reliability determination with the biometric state value and stores the result of the reliability determination and the biometric state value.

20 Claims, 8 Drawing Sheets

BIOMETRIC INFORMATION DETECTING APPARATUS

CROSS-REFERENCE TO RELATED APPLICATION

This application is a U.S. national stage application of International Application No. PCT/JP2005/007990, filed Apr. 27, 2005, claiming a priority date of May 13, 2004, and published in a non-English language.

TECHNICAL FIELD

The present invention relates to a biometric information detecting apparatus for monitoring a state of a living body by measuring biometric information.

BACKGROUND ART

In a background art, there is a pulsimeter for irradiating a light to a living body tissue including the artery, outputting a pulse signal based on a change in a light amount of reflected light or transmitting light of the light in accordance with pulsation of the artery, and measuring a pulse number in a predetermined time period (for example, 1 minute) based on the pulse signal. In order to resolve a problem that although in a case of detecting pulsation optically in this way, no problem is posed when a subject is brought into a rest state, when the subject is moved such that for example, the subject moves the hand or the finger, by being significantly effected with an influence of the physical movement, noise which is unrelated to pulsation is included in the pulse signal (pulse signal), there is known a pulsimeter for preventing a deterioration in an accuracy of measuring (calculating) a pulse number by excluding a value of an interval of generating a pulse signal based on an abnormal pulse signal owing to noise or the like from operation of calculating the pulse number (refer to, for example, patent Reference 1).

Patent Reference 1: JP-A-2002-028139

DISCLOSURE OF THE INVENTION

Problems that the Invention is to Solve

However, according to the pulsimeter shown in Patent Reference 1, information with regard to noise does not remain after finishing the operation and therefore, there poses a problem that data is dealt with similarly even in a case of being measured under a good condition and a case of being otherwise. For example, when the data is not measured necessarily always under what good condition depending on a state of a measured person as in a portable pulsimeter, information of under what good condition the data is measured constitutes important information in viewing a result.

The invention has been carried out in view of such a situation and it is an object thereof to provide a biometric information detecting apparatus for monitoring a state of a living body based on information of adding auxiliary data capable of determining a measured state when measuring living body information to a living body state value.

Means for Solving the Problems

The invention has been carried out in view of the above-described situation. Specifically, the invention described in Claim 1 is characterized in comprising a biometric sensor for measuring biometric information for a predetermined time period, A/D conversion means for acquiring a sampling data by subjecting an output of the biometric sensor to A/D conversion, storing means for storing the sampling data, frequency analyzing means for subjecting the sampling data stored to the storing means to a frequency analysis and storing a result of the analysis to the storing portion, biometric state value calculating means for calculating a biometric state value from the result of the frequency analysis stored to the storing means, SN ratio calculating means for calculating an SN ratio from the result of the frequency analysis stored to the storing means, determining means for determining a reliability of the biometric state value based on whether the SN ratio exceeds a predetermined threshold, and measured data preserving means for correlating to store a result of determining the reliability and the biometric state value.

The invention described in Claim 2 is characterized in further comprising amplifying means having a variable amplification factor for amplifying to output the output of the biometric sensor, amplification factor setting means for setting the amplification factor of the amplifying means, and average amplification factor calculating means for calculating an average amplification factor of the amplification factor set by the amplification factor setting means in the predetermined time period, wherein the determining means outputs an instruction signal for measuring the biometric information again when the average amplification factor exceeds a predetermined threshold.

The invention described in Claim 3 is characterized in further comprising a mounting sensor for detecting whether the biometric sensor is correctly mounted, and mounting rate calculating means for calculating a mounting rate of the biometric sensor within the predetermined time period based on an output of the mounting sensor, wherein the determining means outputs an instruction signal for measuring the biometric information again when the mounting rate exceeds a predetermined threshold.

The invention described in Claim 4 is characterized in further comprising a threshold table in which a threshold for determining the reliability of the biometric state value is defined in accordance with a value of the biometric state value, wherein the determining means reads the threshold in correspondence with the calculated biometric state value from the threshold table and determines the reliability of the biometric state value by using the threshold.

The invention described in Claim 5 is characterized in further comprising peak interval calculating means for calculating all of peak values of the sampling data stored to the storing means and calculating a variation in time intervals among the calculated respective peak values, and a threshold table in which a threshold for determining the reliability of the biometric state value is defined in accordance with a value of a variation in time intervals among the peak values, wherein the determining means reads the threshold in correspondence with the variation of time intervals among the calculated peak values from the threshold table and determines a reliability of the biometric state value by using the threshold.

The invention described in Claim 6 is characterized in further comprising amplifying means having a variable amplification factor for amplifying to output the output of the biometric sensor, amplification factor setting means for setting the amplification factor of the amplifying means, average amplification factor calculating means for calculating an average amplification factor of the amplification factor set by the amplification factor setting means within the predetermined time period, and a threshold table in which a threshold for determining the reliability of the biometric state value is defined in accordance with a value of the biometric state value and a value of the average amplification factor, wherein the determining means reads the threshold in correspondence with the calculated biometric state value and the calculated average amplification factor from the threshold table and determines the reliability of the biometric state value by using the threshold.

The invention described in Claim 7 is characterized in further comprising amplifying means having a variable amplification factor for amplifying to output an output of the biometric sensor, amplification factor setting means for setting the amplification factor of the amplifying means, average amplification factor calculating means for calculating an average amplification factor of the amplification factor set by the amplification factor setting means within the predetermined time period, peak interval calculating means for calculating all of peak values of the sampling data stored to the storing means and calculating a variation in time intervals among the calculated respective peak values, and a threshold table in which a threshold for determining a reliability of the biometric state value is defined in accordance with a value of a variation in the time intervals among the peak values and a value of the average amplification factor, wherein the determining means reads the threshold in correspondence with the variation in the time intervals among the calculated peak values and the calculated average amplification factor and determines the reliability of the biometric state value by using the threshold.

The invention described in Claim 8 is characterized in further comprising a mounting sensor for detecting whether the biometric sensor is correctly mounted, mounting rate calculating means for calculating a mounting rate of the biometric sensor within the predetermined time period based on an output of the mounting sensor, and a threshold table in which a threshold for determining a reliability of the biometric state value is defined in accordance with a value of the biometric state value and a value of the mounting rate, wherein the determining means reads the threshold in correspondence with the calculated biometric state value and the calculated mounting rate from the threshold table and determines the reliability of the biometric state value by using the threshold.

The invention described in Claim 9 is characterized in further comprising a mounting sensor for detecting whether the biometric sensor is correctly mounted, mounting rate calculating means for calculating a mounting rate of the biometric sensor within the predetermined time period based on an output of the mounting sensor, peak interval calculating means for calculating all of peak values of the sampling data stored to the storing means and calculating a variation in time intervals among the calculated respective peak values, and a threshold table in which a threshold for determining the reliability of the biometric state value is defined in accordance with a value of the variation in the time intervals among the peak values and a value of the mounting rate, wherein the determining means reads the threshold in correspondence with the variation in the time intervals among the calculated peak values and the calculated mounting rate from the threshold table and determines the reliability of the biometric state value by using the threshold.

The invention described in Claim 10 is characterized in that the determining means deletes an amount of a predetermined time period of the sampling data from a front thereof when the SN ratio does not exceed the predetermined threshold and outputs an instruction signal for newly measuring to acquire the sampling data of an amount which becomes deficient by the deletion.

The invention described in Claim 11 is characterized in that the determining means further comprising alarming means for outputting an alarm when the SN ratio does not exceed the predetermined threshold.

The invention described in Claim 12 is characterized in further comprising communicating means for communicating information by using a wireless communication, means for measuring the biometric state value based on a measurement schedule received from a server by way of the communicating means, and means for transmitting measurement information correlating a result of determining the reliability and the biometric state value to the server.

The invention described in Claim 13 is characterized in that the biometric information is an artery wave and the biometric state value is a pulse number.

The invention described in Claim 14 is characterized in a biometric information detecting system comprising a biometric information detecting apparatus for measuring a biometric state value by being attached to a physical body of a measured person, and a biometric information processing server for carrying out a predetermined processing by receiving the biometric state value measured by the biometric information detecting apparatus by way of a wireless communication, wherein the biometric information detecting apparatus comprises a biometric sensor for measuring biometric information for a predetermined time period, A/D conversion means for acquiring a sampling data by subjecting an output of the biometric sensor to A/D conversion, storing means for storing the sampling data, frequency analyzing means for subjecting the sampling data stored to the storing means to a frequency analysis and storing a result of the analysis to the storing portion, biometric state value calculating means for calculating a biometric state value from the result of the frequency analysis stored to the storing means, SN ratio calculating means for calculating an SN ratio from the result of the frequency analysis stored to the storing means, and communicating means for transmitting the biometric state value and the SN ratio to the biometric information processing server, and wherein the biometric information processing server comprises communicating means for receiving the biometric state value and the SN ratio from the biometric information detecting apparatus, determining means for determining a reliability of the biometric state value based on whether the SN ratio exceeds a predetermined threshold, and measured data preserving means for correlating to store a result of determining the reliability and the biometric state value.

The invention described in Claim 15 is characterized in a biometric information detecting apparatus for transmitting a biometric state value measured by being attached to a physical body of a measured person to a biometric information processing server for carrying out a predetermined processing by way of a wireless communication, the biometric information detecting apparatus comprising a biometric sensor for measuring biometric information for a predetermined time period, A/D conversion means for acquiring a sampling data by subjecting an output of the biometric sensor to A/D conversion, storing means for storing the sampling data, frequency analyzing means for subjecting the sampling data stored to the storing means to a frequency analysis and storing a result of the analysis to the storing portion, biometric state value calculating means for calculating the biometric state value from the result of the frequency analysis stored to the storing means, SN ratio calculating means for calculating an SN ratio from the result of the frequency analysis stored to the storing means, and communicating means for transmitting the biometric state value and the SN ratio to the biometric information processing server.

The invention described in Claim 16 is characterized in a biometric information processing server characterized in a biometric information processing server for receiving a biometric state value measured by attaching a biometric information detecting apparatus to a physical body of a measured person by way of a wireless communication and carrying out a predetermined processing, the biometric information processing server comprising communicating means for receiving the biometric state value and the SN ratio from the biometric information detecting apparatus, determining means for determining a reliability of the biometric state value based on whether the SN ratio exceeds a predetermined threshold, and measured data preserving means for correlating to store a result of determining the reliability and the biometric state value.

The invention described in Claim 17 is characterized in a biometric information detecting method in a biometric information detecting apparatus comprising a biometric sensor for measuring biometric information for a predetermined timed period, A/D conversion means for acquiring a sampling data by subjecting an output of the biometric sensor to A/D conversion, storing means for storing the sampling data, and measured data preserving means for storing a data of a measurement result, the biometric information detecting method comprising a frequency analyzing procedure for subjecting the sampling data stored to the storing means to a frequency analysis and storing a result of the analysis to the storing portion, a biometric state value calculating procedure for calculating a biometric state value from the result of the frequency analysis stored to the storing means, an SN ratio calculating procedure for calculating an SN ratio from the result of the frequency analysis stored to the storing means, a determining procedure of determining a reliability of the biometric state value based on whether the SN ratio exceeds a predetermined threshold, and a measured data preserving procedure for correlating a result of determining the reliability and the biometric state value to be stored to the measured data preserving means.

The invention described in Claim 18 is characterized in further comprising a biometric information detecting method in a biometric information detecting system comprising (a) a biometric information detecting apparatus comprising a biometric sensor for measuring biometric information for a predetermined time period, A/D conversion means for acquiring a sampling data by subjecting an output of the biometric sensor to A/D conversion, storing means for storing the sampling data, and communicating means for transmitting the calculated biometric state value and an SN ratio for measuring the biometric state value by being attached to a physical body of a measured person, and (b) a biometric information processing server comprising communicating means for receiving the biometric state value and the SN ratio measured by the biometric information detecting apparatus, and measured data preserving means for storing a data of a measurement result, wherein the biometric information detecting apparatus comprises a frequency analyzing procedure of subjecting the sampling data stored to the storing means to a frequency analysis and storing a result of the analysis to the storing portion, a biometric state value calculating procedure of calculating the biometric state value from the result of the frequency analysis stored to the storing means, and an SN ratio calculating procedure of calculating the SN ratio from the result of the frequency analysis stored to the storing means, and wherein the biometric information processing server comprises a determining procedure of determining a reliability of the biometric state value based on whether the SN ratio exceeds a predetermined threshold, and a measured data preserving procedure of correlating a result of determining the reliability and the biometric state value to be stored to the measured data preserving means.

BEST MODE FOR CARRYING OUT THE INVENTION

Figure 1:
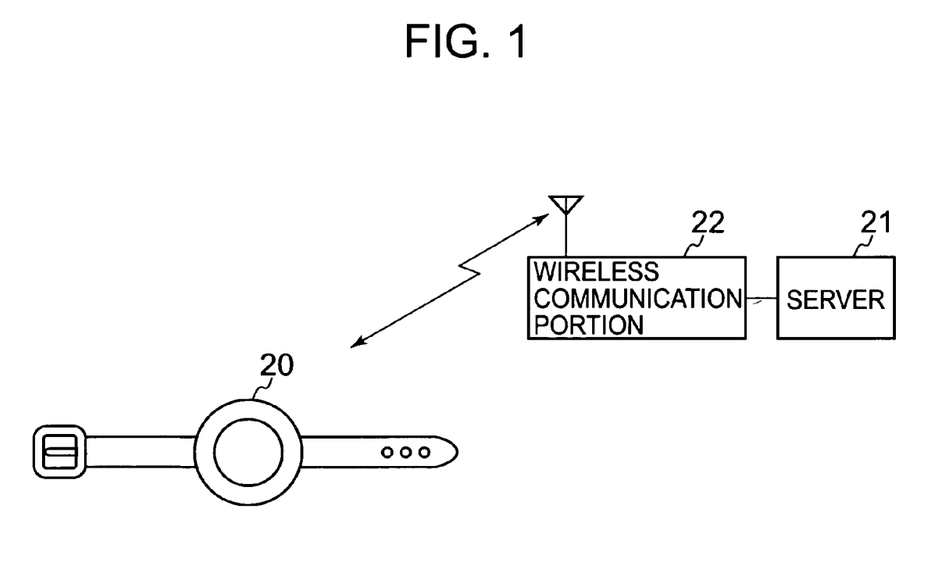
FIG. 1 is a block diagram showing a total constitution of an embodiment of the invention.

An explanation will be given of a biometric information detecting apparatus according to an embodiment of the invention in reference to the drawings as follows. FIG. 1 is a block diagram showing a total constitution of the embodiment. In the drawing, notation 20 designates a biometric information detecting apparatus of a wristwatch type for measuring pulsation based on a previously determined measurement schedule. Notation 21 designates a server for collecting biometric information measured by the biometric information detecting apparatus 20. Notation 22 designates a wireless communication portion for receiving biometric information measured by the biometric information detecting apparatus 20 by using wireless communication to deliver to the server 21.

Figure 2:
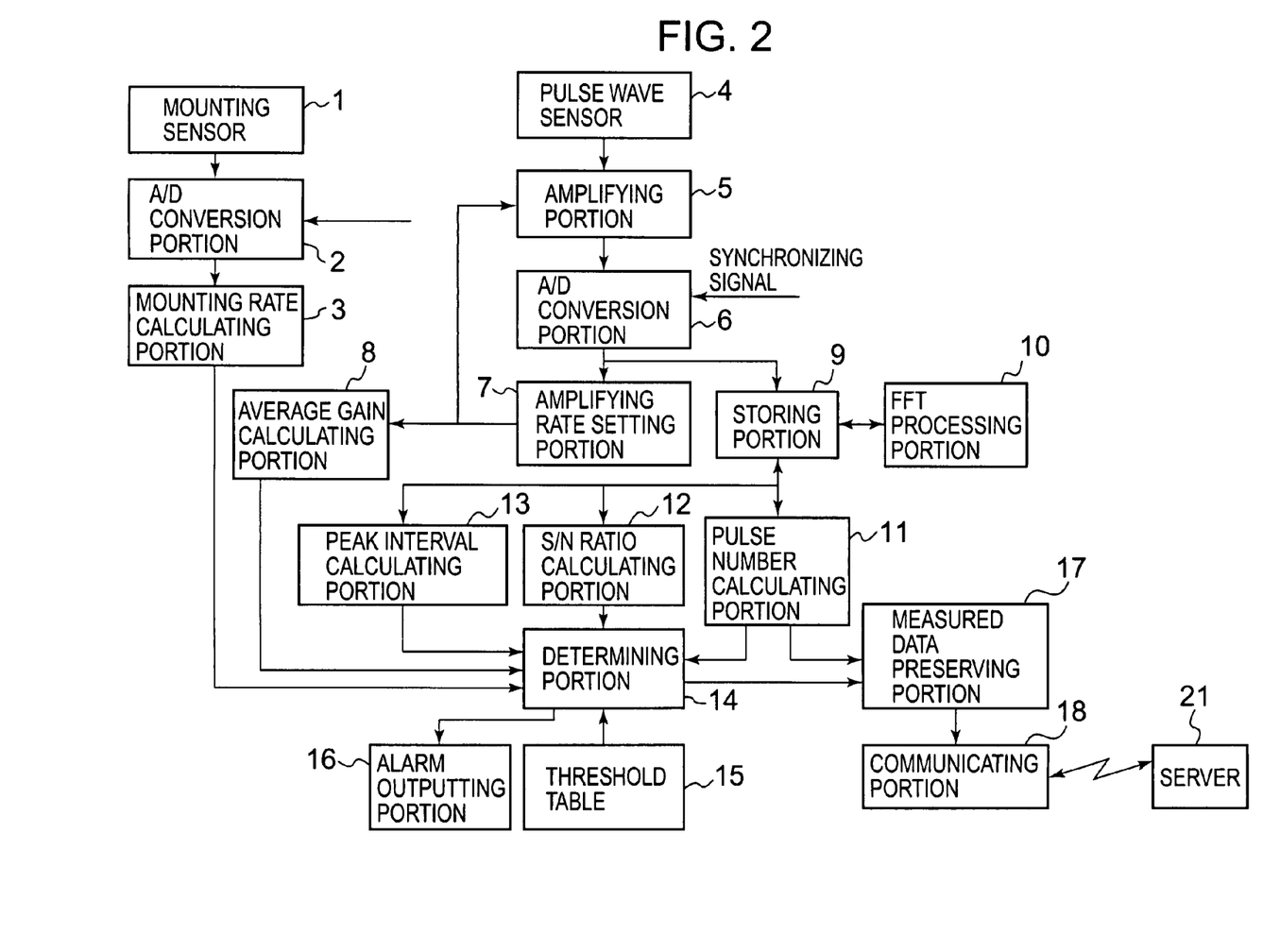
FIG. 2 is a block diagram showing a constitution of a biometric information detecting apparatus 20 shown in FIG. 1.

Next, a constitution of an essential portion of the biometric information detecting apparatus 20 shown in FIG. 1 will be explained in reference to FIG. 2. FIG. 2 is a block diagram showing a constitution of the biometric information detecting apparatus 20 shown in FIG. 1. In the drawing, notation 1 designates a mounting sensor for detecting a state of mounting the biometric information detecting apparatus 20 of the wristwatch type to the wrist of a measured person. Notation 2 designates an A/D conversion portion for converting an output of the mounting sensor 1 into a digital value. Notation 3 designates a mounting rate calculating portion for calculating a mounting rate within a predetermined time period based an output of the mounting sensor 1. Notation 4 designates a pulse wave sensor for detecting living body information of a measured person and various sensors of an optical sensor, a piezoelectric element and the like are used therefor in accordance with a detecting system. Notation 5 designates an amplifying portion for amplifying an output signal of the electroencephalogram sensor 4, and an amplification factor thereof can arbitrarily be changed. Notation 6 designates an A/D conversion portion for converting an output signal of the pulse wave sensor 4 amplified by the amplifying portion 5 into a digital value to provide sampling data. Notation 7 designates an amplification factor setting portion for setting an amplification factor of the amplifying portion 5. Notation 8 designates an average gain calculating portion for calculating an average value of the amplification factor (referred to as average gain) set by the amplification factor setting portion 7. Notation 9 designates a storing portion for storing the sampling data outputted by the A/D conversion portion 6. Notation 10 designates an FFT processing portion for subjecting the sampling data stored to the storing portion 9 to frequency analysis by using FFT (Fast Fourier Transform) and storing a result of the analysis to the storing portion 9. Notation 11 designates a pulse number calculating portion for calculating a pulse number based on a result of the frequency analysis of the sampling data.

Notation 12 designates an S/N ratio calculating portion for calculating an SN ratio of the sampling data based on the result of the frequency analysis of the sampling data. Notation 13 designates a peak interval calculating portion for calculating all of peak values of the sampling data stored to the storing portion 9 and calculating a variation in time intervals among the calculated respective peak values. Notation 14 designates a determining portion for determining reliability of a calculated pulse number based on whether the calculated SN ratio exceeds a predetermined ratio. Notation 15 designates a threshold table previously stored with the threshold for determining whether the calculated SN ratio exceeds the threshold. Notation 16 designates an alarm outputting portion for issuing an alarm based on a result of determination of the determining portion 14. Notation 17 designates a measured data reserving portion for generating to store the result of determination of reliability at the determining portion 14 and the calculated pulse number. Notation 18 designates a communicating portion for establishing information communication between the communicating portion and the wireless communication portion 22, transmitting the result of determination of the reliability and the calculated pulse number stored to the measured data preserving portion 17 and receiving a measurement schedule from the server 21.

Figure 3:
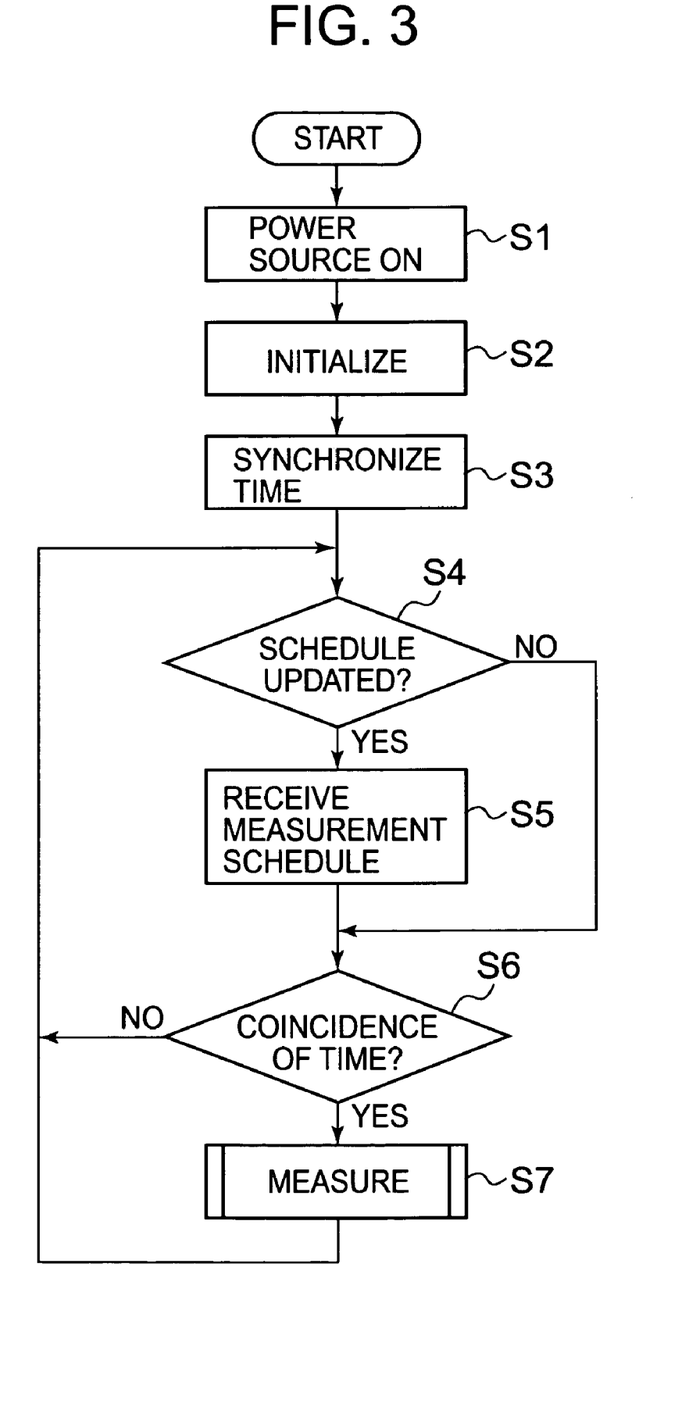
FIG. 3 is a flowchart showing operation of the biometric information detecting apparatus 20 shown in FIG. 1.

Next, an explanation will be given of a basic operation of measuring pulsation by the biometric information detecting apparatus 20 shown in FIG. 1 in reference to FIG. 3. FIG. 3 is a flowchart showing the basic operation of the biometric information detecting apparatus 20 shown in FIG. 1. First, when a power source of the biometric information detecting apparatus 20 attached to the wrist of a measured person is made ON (step S1), the storing portion 9 and the measured data preserving portion 17 at inside of the biometric information detecting apparatus 20 is initialized (step S2). Successively, the communicating portion 18 synchronizes time of schedule controlling timers (not illustrated) at inside of the server 21 and the biometric information detecting apparatus 20 by receiving current time data from the server 21 (step S3).

Next, the communicating portion 18 inquires whether the measurement schedule is updated to the server 21 and receives the measurement schedule when updated (steps S4, S5). The measurement schedule mentioned here is data comprising measurement time of an amount of one day and is defined with time of measuring pulsation such that, for example, '8:00, 9:00, 10:00, . . . , 21:00'. The measurement schedule is preserved in a memory provided to the biometric information detecting apparatus 20 and is not erased even when the power source is made OFF, and a content thereof remains unchanged unless the measurement schedule is updated. The timer at inside of the biometric information detecting apparatus 20 checks the current time and the measurement schedule and measures pulsation when measurement time is reached (steps S6, S7).

Figure 4:
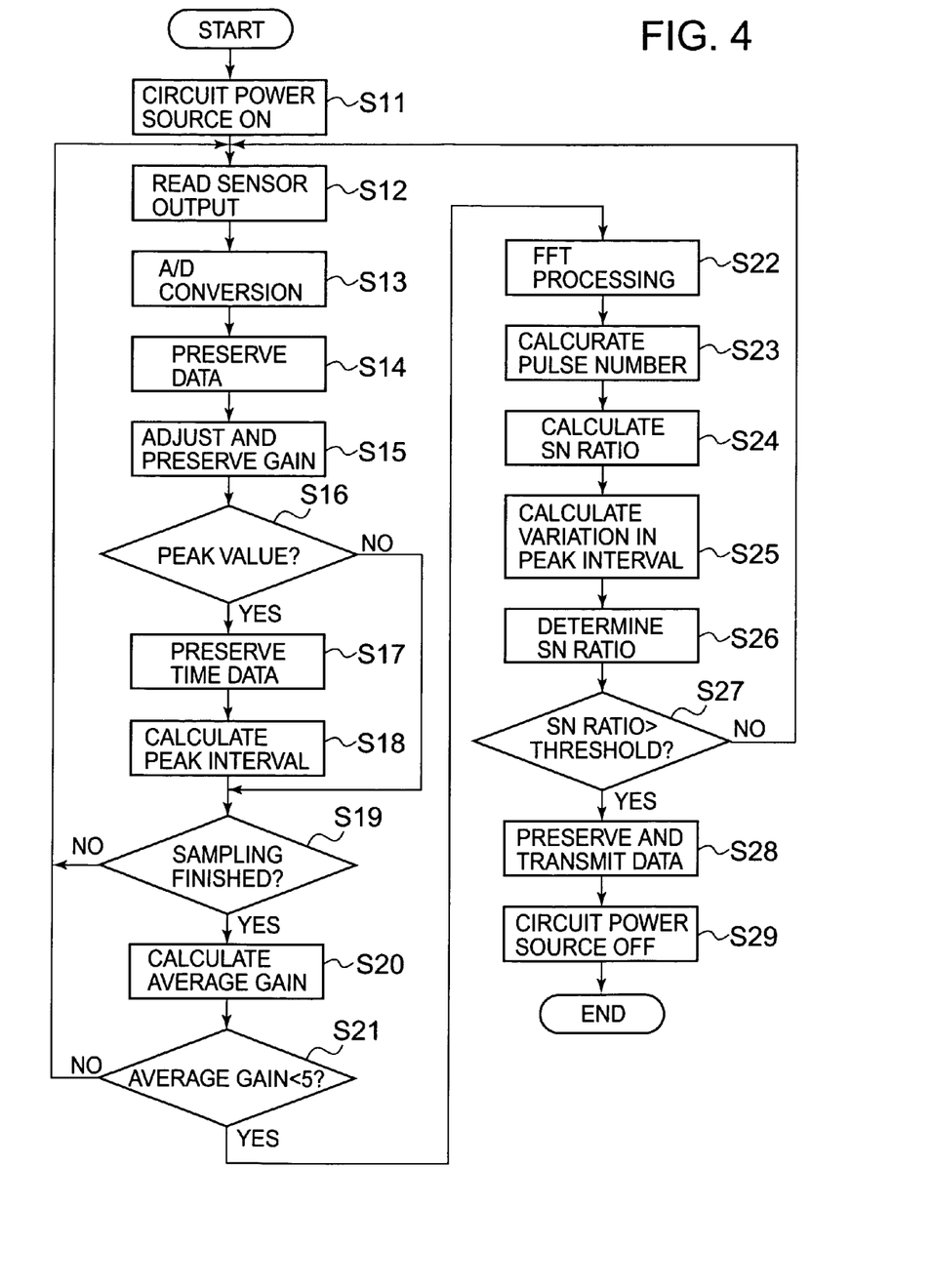
FIG. 4 is a flowchart showing operation of the biometric information detecting apparatus 20 shown in FIG. 1.

Next, details of a measuring operation (step S7) shown in FIG. 3 will be explained in reference to FIG. 4. FIG. 4 is a flowchart showing a detailed operation of the measuring operation (step S7) shown in FIG. 3. First, at time point of reaching the measurement time, a circuit power source is made ON (step S11). The circuit power source is brought into an OFF state at other than the measurement time and is made ON at time point of reaching the measurement time based on an instruction from the schedule controlling timer.

Next, the amplifying portion 5 reads the output signal of the pulse wave sensor 4 and amplifies the output signal to be outputted to the A/D conversion portion 6 (step S12). The A/D conversion portion 6 acquires the sampling data by sampling the output signal of the amplifying portion 5 to be converted by A/D conversion (step S13). The sampling data is stored to the storing portion 9 (step S14).

On the other hand, the amplification factor setting portion 7 adjusts the amplification factor of the amplifying portion 5 based on a sampling data after having been subjected to A/D conversion, and outputs the set amplification factor to the average gain calculating portion 8. By receiving the amplification factor, the average gain calculating portion 8 preserves the amplification factor at inside thereof (step S15).

Next, the peak interval calculating portion 13 determines whether the newest sampling data stored to the storing portion 9 is a peak value (step S16). When the newest sampling data is a peak value as a result of the determination, time data of the sampling data is preserved at inside thereof (step S17). The time data mentioned here is an elapsed time period after starting the sampling and corresponds to sampling interval time period×(number of data −1). Further, the peak interval calculating portion 13 calculates a peak interval (step S18).

Figure 6:
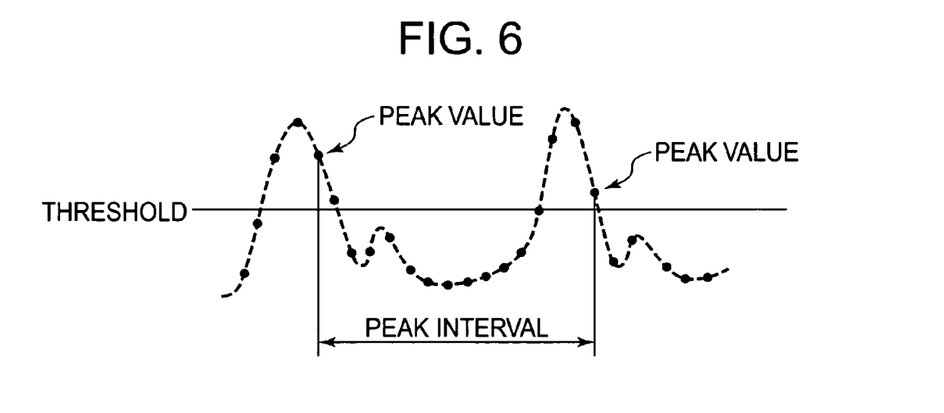
FIG. 6 is an explanatory diagram showing a method of calculating a peak interval.

An explanation will be given here of the peak interval in reference to FIG. 6. The peak value is a sampling data when a value of a newly acquired sampling data is smaller than a value of a sampling data one data before and the value of the newly acquired sampling data is larger than a previously determined threshold. The peak interval is a time period between the peak values. According to the example of FIG. 6, two peak values are present and a time period therebetween is the peak interval.

When the processings of steps S12 through S18 are repeatedly executed at a predetermined sampling period (8 Hz: 125 ms interval) for a predetermined time period (for example, 16 seconds) (step S19), the storing portion 9 is stored with 128 pieces of sampling data, the peak intervals among the peak values are preserved at inside of the peak interval calculating portion 13, and the set value of the amplification factor is preserved at inside of the average gain calculating portion 8.

Next, the average gain calculating portion 8 calculates average gain data by calculating an average of the set values of the amplification factors preserved at in side thereof (step S20), and outputs the average gain data to the determining portion 14. The determining portion 14 compares the inputted average gain data with a predetermined threshold (for example, '5') (step S21), determines that the reliability of the acquired sampling data is low when the average gain data exceeds the threshold and outputs an instruction signal for instructing measurement again to the amplifying portion 5 and the A/D conversion portion 6. Thereby, the measurement processing is executed again.

On the other hand, when the average gain does not exceed the threshold, the determining portion 14 outputs an instruction signal of executing the frequency analysis to the FFT processing portion 10. By receiving the instruction signal, the FFT processing portion 10 executes the frequency analysis of the sampling data stored to the storing portion 9 (step S22). Thereby, a frequency of a main component of the sampling data is acquired. The FFT processing portion 10 stores the acquired result of the frequency analysis to the storing portion 9.

Figure 7:
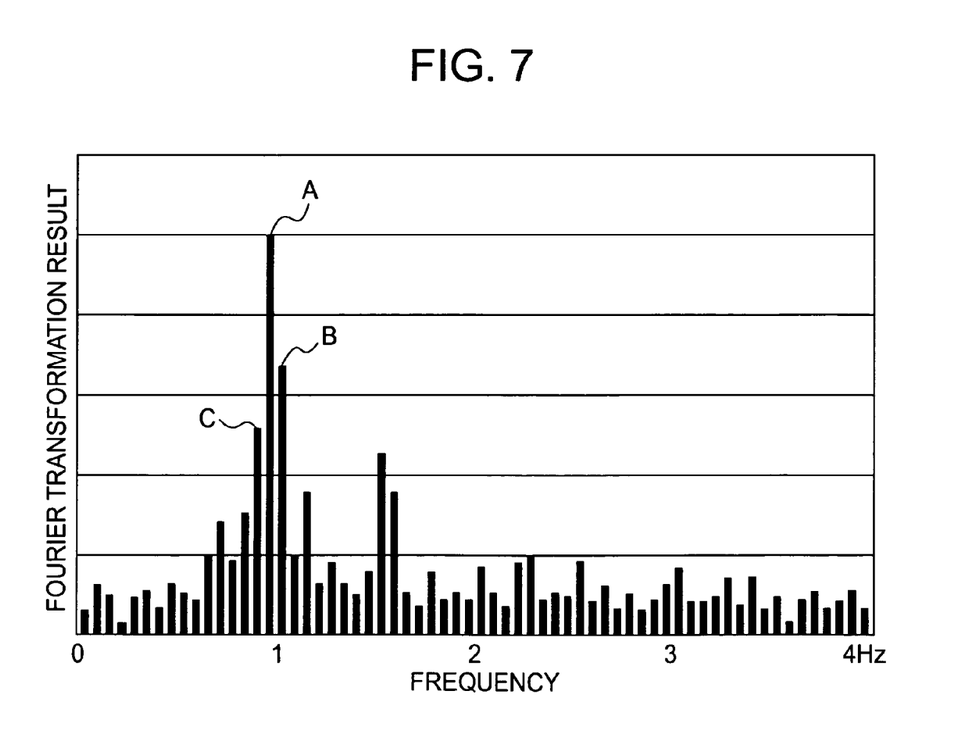
FIG. 7 is an explanatory diagram showing an FFT processing result.

Next, the pulse number calculating portion 11 calculates the pulse number from the value of the frequency of the main component of the sampling data stored to the storing portion 9 to output to the determining portion 14 (step S23) at time point of finishing the frequency analysis processing. In parallel therewith, the S/N ratio calculating portion 12 calculates the SN ratio from the result of the frequency analysis to be outputted to the determining portion 14 at time point of finishing the frequency analysis processing (step S24). A result of the frequency analysis analyzed by the FFT processing portion 10 becomes as shown by FIG. 7. The SN ratio is calculated by divining (a sum of heights of a base line (notation A) in correspondence with the pulse signal and base lines (notations B, C) therebefore and thereafter) by (a sum of heights of all base lines). Further, the peak interval calculating portion 13 calculates a variation in values of peak intervals preserved at inside thereof (step S25) to be outputted to the determining portion 14. Further, the mounting rate calculating portion 3 calculates the mounting rate from data constituted by subjecting an output signal of the mounting sensor 1 to A/D conversion to be outputted to the determining portion 14. Thereby, the determining portion 14 is inputted with the data of the average gain, the data of the pulse number, the data of the SN ratio, the data of the variation in the peak interval values, and the data of the mounting rate.

Next, the determining portion 14 determines the SN ratio (step S26). At this occasion, the determining portion 14 compares the threshold stored to the threshold table 15 with the SN ratio and determines whether the SN ratio is larger than the threshold (step S27). Further, when the SN ratio is larger than the threshold, it is determined that the reliability of the calculated pulse number is high, and when the SN ratio is smaller than the threshold, it is determined that the reliability of the calculated pulse number is low.

An explanation will be given here of the threshold described in the threshold table 15 in reference to FIG. 5. The threshold table 15 is stored with four of threshold tables (a), (b), (c) and (d) in advance.

Figure 5A:
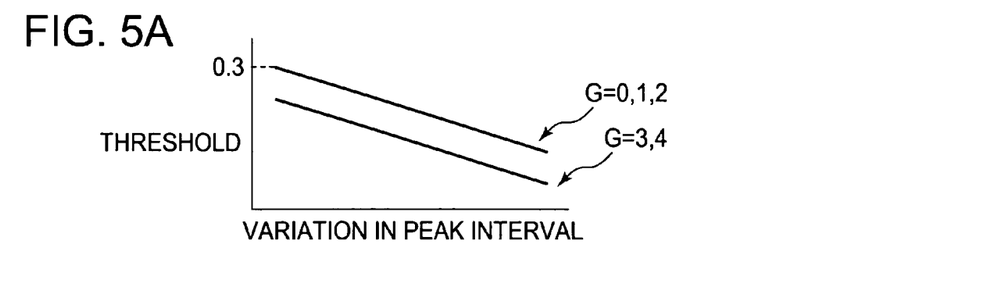
FIG. 5 illustrates explanatory views showing an example of a threshold table 15 shown in FIG. 2.

The threshold table shown in FIG. 5(a) is defined such that the larger the variation in the peak interval, the smaller the threshold of the SN ratio, further defining curves which differ in a case of the average gain G of '0, 1, 2' and a case of the average gain G of '3, 4'.

Figure 5B:
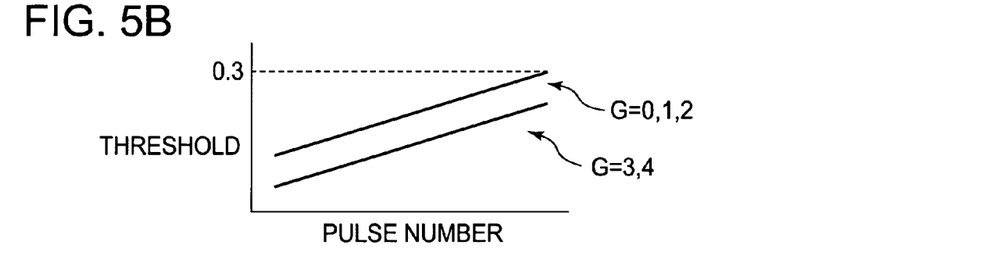

The threshold table shown in FIG. 5(b) is defined such that the larger the pulse number, the larger the threshold of the SN ratio, further defining thresholds which differ in a case of the average gain G of '0, 1, 2' and a case of the average gain G of '3, 4'.

Figure 5C:
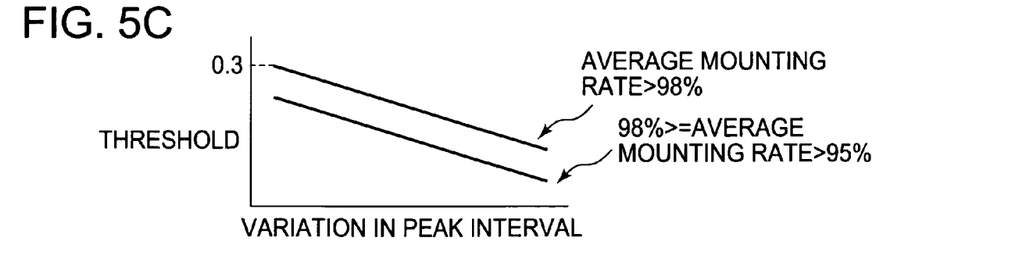

The threshold table shown in FIG. 5(c) is defined such that the larger the variation in the peak interval, the smaller the threshold of the SN ratio, further defining thresholds which differ in a case of an average mounting rate equal to or larger than 98%, and a case of the average mounting rate of 95 through 98%.

Figure 5D:
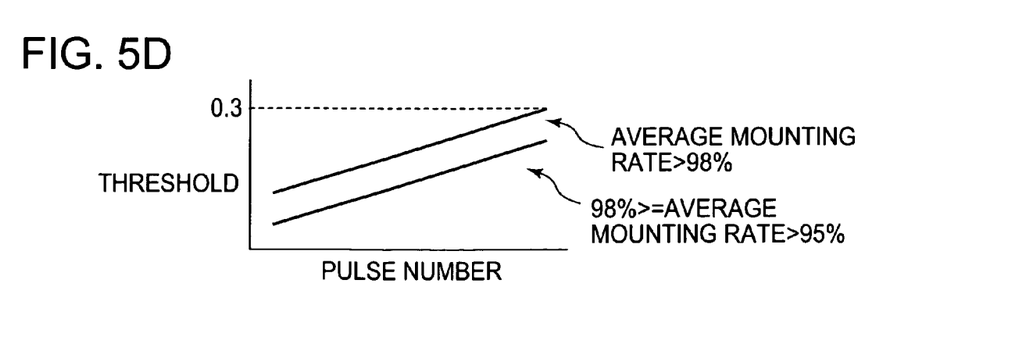

The threshold table shown in FIG. 5(d) is defined such that the larger the pulse number, the larger the threshold of the SN ratio, further defining thresholds which differ in a case of an average mounting rate equal to or larger than 98% and a case of the average mounting rate of 95 through 98%.

The determining portion 14 selects the threshold table used for determining the threshold based on the instruction of the server 21 and determines the SN ratio in reference to the selected threshold table. For example, when the threshold table used is the table of (b) shown in FIG. 5, the determining portion 14 reads the threshold of the SN ratio in correspondence with the pulse number and the average gain inputted, and compares large or small of the threshold and the calculated SN ratio to determine the reliability.

Next, the determining portion 14 outputs an instruction signal to the alarm outputting portion 16 to issue an alarm when the reliability is determined to be low. By receiving the instruction signal, the alarm outputting portion 16 emits alarm sound. The alarm sound urges the measured person to bring the pulse wave sensor 4 into close contact with the skin. Further, the determining portion 14 outputs an instruction signal of instructing the measurement again to the amplifying portion 5 and the A/D conversion portion 6 when the reliability is determined to be low. Thereby, the measuring processing is executed again.

On the other hand, when the reliability is determined to be high, the determining portion 14 correlates the data of the average gain, the data of the pulse number, the data of the SN ratio, the data of the variation in the peak interval values and the data of the mounting rate, information indicating the high reliability, and the measurement time which are inputted to preserve in the measurement data preserving portion 17. The communicating portion 18 establishes communication with the server 21 upon preserving the data to the measured data preserving portion 17 and transmits the data preserved in the measured data preserving portion 17 to the server 21 (step S28). Further, the circuit power source is made OFF (step S29).

Figure 9:
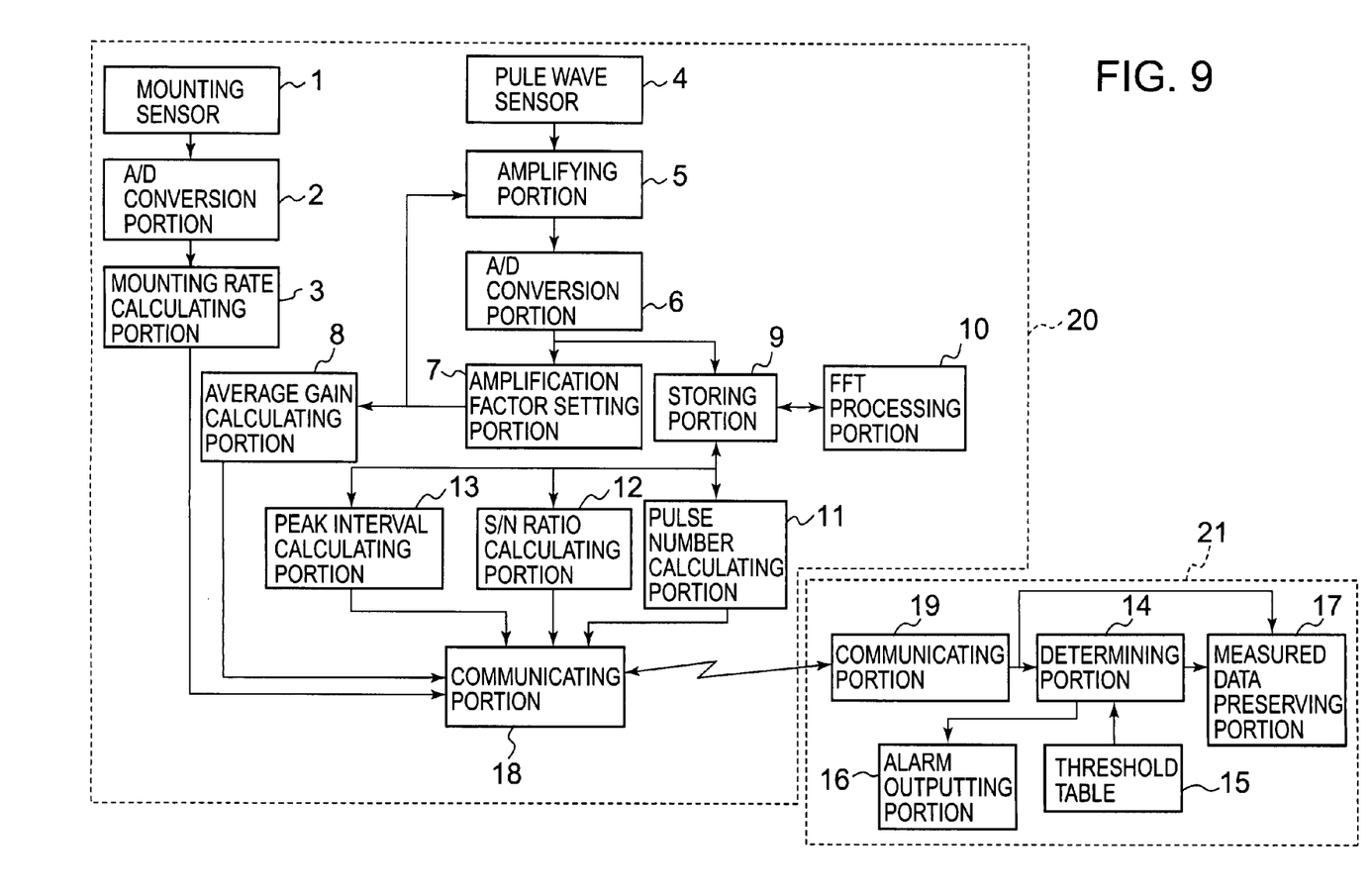
FIG. 9 is a block diagram showing a constitution of other embodiment of the invention.

Next, other embodiment will be explained in reference to FIG. 9. A constitution shown in FIG. 9 is provided with the determining portion 14, the threshold table 15, the alarm outputting portion 16 and the measured data preserving portion 17 at inside of the server 21. The biometric information detecting apparatus 20 transmits the pulse number, the SN ratio, the variation in the peak interval, and the average gain which are calculated to the server 21 by way of the communicating portion 18. The server 21 determines the reliability of the pulse number based on the pulse number, the SN ratio, the variation in the peak interval, the average gain which are received. In this case, an alarm outputting portion may be provided also at inside of the biometric information detecting apparatus 20, and when the reliability is determined to be low and the measurement is carried out again, an instruction of issuing alarm sound may be outputted from the server 21 to the alarm outputting portion at inside of the biometric information detecting apparatus 20. Other detailed operation thereof is similar to the above-described operation and therefore, a detailed explanation will be omitted here.

In this way, it can be determined whether the data is reliable in observing the measurement data at a later stage by simultaneously observing also supplementary data. For example, in a case of abruptly changing the measured value, when also the supplementary data is changed abruptly, it can be determined that a measurement condition is not acceptable.

Further, although at steps S20, S21 shown in FIG. 4, based on the value of the average gain, it is determined whether the measurement is carried out again, based on the mounting rate, the measurement may be carried out again when the mounting rate is low.

Further, it is not necessary to provide all of four tables in the threshold table 15 but only a necessary table may be stored. At this occasion, only a necessary one of the data inputted to the determining portion 14 may be inputted and therefore, it is not necessary to provided all of constituent elements shown in FIG. 2 at inside of the biometric information detecting apparatus 20 but a necessary minimum constitution for acquiring data necessary for determination may be provided.

Figure 8:
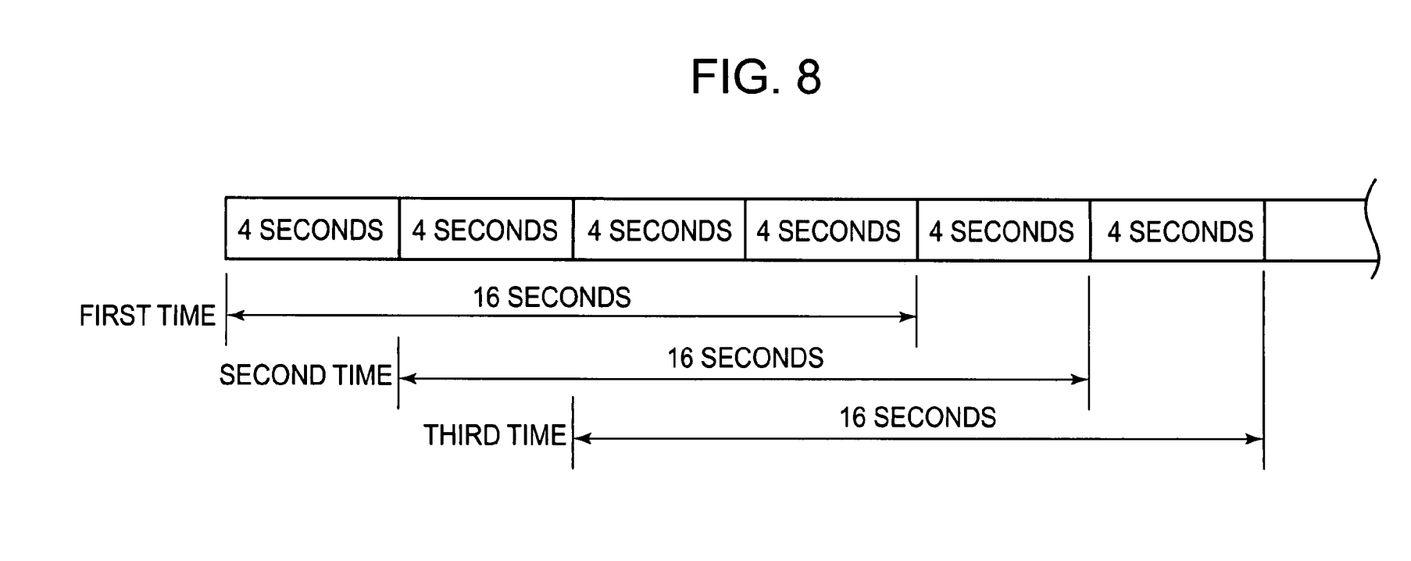
FIG. 8 is an explanatory diagram showing a timing of data sampling.

Further, when the measurement is carried out again based on the result of determination, as shown by FIG. 8, in the first sampling data, an amount of front 4 seconds may be deleted, in second measurement, only an amount of deficient 4 seconds may be measured. Further, also in a third measurement, only an amount of deficient 4 seconds may be measured. Thereby, power consumption of the power source in measuring again can be restrained.

Further, although according to the above-described embodiments, an explanation has been given by using an example of measuring the pulse number, not only the pulse number but also other state related to the living body may be measured.

Further, the biometric information detecting processing may be carried out by recording a program for realizing functions of the respective processing portions in FIG. 2 to a computer readable record medium, reading the program recorded on the record medium by a computer system, and executing the program. Further, the 'computer system' mentioned here includes OS and a hardware of a peripheral apparatus or the like. Further, the 'computer readable record medium' refers to a portable medium of a flexible disk, a photomagnetic disk, ROM, CD-ROM or the like, or a storing apparatus of a hard disk or the like included in the computer system. Further, the 'computer readable record medium' includes also a medium holding the program for a constant period of time such as a server when the program is transmitted by way of a network of the internet or the like or a communication network of a telephone network or the like, or an involatile memory (RAM) at inside of the computer system constituting a client.

Further, the program may be transmitted from a computer system storing the program to a storing apparatus or the like to other computer system from a computer system stored with the program in the storing apparatus or the like by way of a transmission medium, or a transmission wave in the transmission medium. Here, the 'transmission medium' for transmitting the program refers to a medium having a function of transmitting information such as a network (communication network) of the internet or the like, or a communication network (communication line) of a telephone network or the like. Further, the program may be for realizing a portion of the above-described functions. Further, the transmission medium may be a so-to-speak difference file (difference program) capable of realizing the above-described functions in combination with a program already stored to the computer system.

INDUSTRIAL APPLICABILITY

According to the invention, in observing the measurement data at later stage, it can be determined whether the data is reliable by simultaneously observing also supplementary data. Further, the measurement is carried out again based on a result of comparing with the predetermined threshold and therefore, highly reliable biometric information can firmly be measured.

The invention claimed is:

1. A biometric information detecting apparatus comprising:
    a biometric sensor for measuring biometric information for a predetermined time period;
    A/D conversion means for acquiring a sampling data by subjecting an output of the biometric sensor to A/D conversion;
    storing means for storing the sampling data;
    frequency analyzing means for subjecting the sampling data stored to the storing means to a frequency analysis and storing a result of the frequency analysis to the storing means;
    biometric state value calculating means for calculating a biometric state value from the result of the frequency analysis stored to the storing means;
    SN ratio calculating means for calculating an SN ratio from the result of the frequency analysis stored to the storing means;
    determining means for determining a reliability of the biometric state value based on whether the calculated SN ratio exceeds a predetermined threshold; and
    measured data storing means for associating a result of the reliability determination with the biometric state value and storing the result of the reliability determination and the biometric state value.

2. A biometric information detecting apparatus according to claim 1; further comprising:
    amplifying means having a variable amplification factor for amplifying to output the output of the biometric sensor;
    amplification factor setting means for setting the amplification factor of the amplifying means; and
    average amplification factor calculating means for calculating an average amplification factor of the amplification factor set by the amplification factor setting means in the predetermined time period;
    wherein the determining means outputs an instruction signal for measuring the biometric information again when the average amplification factor exceeds a predetermined threshold.

3. A biometric information detecting apparatus according to claim 1; further comprising:
    a mounting sensor for detecting whether the biometric sensor is correctly mounted; and
    mounting rate calculating means for calculating a mounting rate of the biometric sensor within the predetermined time period based on an output of the mounting sensor;
    wherein the determining means outputs an instruction signal for measuring the biometric information again when the mounting rate exceeds a predetermined threshold.

4. A biometric information detecting apparatus according to claim 1; further comprising:
    a threshold table in which a threshold for determining the reliability of the biometric state value defined in accordance with a value of the biometric state value;
    wherein the determining means reads the threshold in correspondence with the calculated biometric state value from the threshold table and determines the reliability of the biometric state value by using the threshold.

5. A biometric information detecting apparatus according to claim 1; further comprising:
    peak interval calculating means for calculating all of peak values of the sampling data stored to the storing means and calculating a variation in time intervals among the calculated respective peak values; and
    a threshold table in which a threshold for determining the reliability of the biometric state value is defined in accordance with a value of a variation in time intervals among the peak values;
    wherein the determining means reads the threshold in correspondence with the variation of time intervals among the calculated peak values from the threshold table and determines a reliability of the biometric state value by using the threshold.

6. A biometric information detecting apparatus according to claim 1; further comprising:
amplifying means having a variable amplification factor for amplifying to output the output of the biometric sensor;
amplification factor setting means for setting the amplification factor of the amplifying means;
average amplification factor calculating means for calculating an average amplification factor of the amplification factor set by the amplification factor setting means within the predetermined time period; and
a threshold table in which a threshold for determining the reliability of the biometric state value is defined in accordance with a value of the biometric state value and a value of the average amplification factor;
wherein the determining means reads the threshold in correspondence with the calculated biometric state value and the calculated average amplification factor from the threshold table and determines the reliability of the biometric state value by using the threshold.

7. A biometric information detecting apparatus according to claim 1; further comprising:
amplifying means having a variable amplification factor for amplifying to output an output of the biometric sensor;
amplification factor setting means for setting the amplification factor of the amplifying means;
average amplification factor calculating means for calculating an average amplification factor of the amplification factor set by the amplification factor setting means within the predetermined time period;
peak interval calculating means for calculating all of peak values of the sampling data stored to the storing means and calculating a variation in time intervals among the calculated respective peak values; and
a threshold table in which a threshold for determining a reliability of the biometric state value is defined in accordance with a value of a variation in the time intervals among the peak values and a value of the average amplification factor;
wherein the determining means reads the threshold in correspondence with the variation in the time intervals among the calculated peak values and the calculated average amplification factor and determines the reliability of the biometric state value by using the threshold.

8. A biometric information detecting apparatus according to claim 1; further comprising:
a mounting sensor for detecting whether the biometric sensor is correctly mounted;
mounting rate calculating means for calculating a mounting rate of the biometric sensor within the predetermined time period based on an output of the mounting sensor; and
a threshold table in which a threshold for determining a reliability of the biometric state value is defined in accordance with a value of the biometric state value and a value of the mounting rate;
wherein the determining means reads the threshold in correspondence with the calculated biometric state value and the calculated mounting rate from the threshold table and determines the reliability of the biometric state value by using the threshold.

9. A biometric information detecting apparatus according to claim 1; further comprising:
a mounting sensor for detecting whether the biometric sensor is correctly mounted;
mounting rate calculating means for calculating a mounting rate of the biometric sensor within the predetermined time period based on an output of the mounting sensor;
peak interval calculating means for calculating all of peak values of the sampling data stored to the storing means and calculating a variation in time intervals among the calculated respective peak values; and
a threshold table in which a threshold for determining the reliability of the biometric state value is defined in accordance with a value of the variation in the time intervals among the peak values and a value of the mounting rate;
wherein the determining means reads the threshold in correspondence with the variation in the time intervals among the calculated peak values and the calculated mounting rate from the threshold table and determines the reliability of the biometric state value by using the threshold.

10. A biometric information detecting apparatus according to claim 1; wherein the determining means deletes an amount of predetermined time period of the sampling data from a front thereof when the SN ratio does not exceed the predetermined threshold and outputs an instruction signal for newly measuring to acquire the sampling data of an amount which becomes deficient by the deletion.

11. A biometric information detecting apparatus according to claim 1; wherein the determining means comprises alarming means for outputting an alarm when the SN ratio does not exceed the predetermined threshold.

12. A biometric information detecting system comprising:
a biometric information detecting apparatus for measuring a biometric state value by being attached to a physical body of a measured person, the biometric information detecting apparatus comprising:
a biometric sensor for measuring biometric information for a predetermined time period;
A/D conversion means for acquiring a sampling data by subjecting an output of the biometric sensor to A/D conversion;
storing means for storing the sampling data;
frequency analyzing means for subjecting the sampling data stored to the storing means to a frequency analysis and storing a result of the frequency analysis to the storing means;
biometric state value calculating means for calculating a biometric state value from the result of the frequency analysis stored to the storing means;
SN ratio calculating means for calculating an SN ratio from the result of the frequency analysis stored to the storing means; and
communicating means for transmitting the biometric state value and the SN ratio; and
a biometric information processing server for carrying out a predetermined processing by receiving the biometric state value measured by the biometric information detecting apparatus by way of a wireless communication, the biometric information processing server comprising:
communicating means for receiving the biometric state value and the SN ratio transmitted from the biometric information detecting apparatus;
determining means for determining a reliability of the biometric state value based on whether the calculated SN ratio exceeds a predetermined threshold; and
measured data storing means for associating a result of the reliability determination with the biometric state value and storing the result of the reliability determination and the biometric state value.

13. A biometric information detecting apparatus for transmitting a biometric state value measured by being attached to a physical body of a measured person to a biometric information processing server for carrying out a predetermined processing by way of a wireless communication, the biometric information detecting apparatus comprising:
   a biometric sensor for measuring biometric information for a predetermined time period;
   A/D conversion means for acquiring a sampling data by subjecting an output of the biometric sensor to A/D conversion;
   storing means for storing the sampling data;
   frequency analyzing means for subjecting the sampling data stored to the storing means to a frequency analysis and storing a result of the frequency analysis to the storing means;
   biometric state value calculating means for calculating a biometric state value from the result of the frequency analysis stored to the storing means;
   SN ratio calculating means for calculating an SN ratio from the result of the frequency analysis stored to the storing means; and
   communicating means for transmitting the biometric state value and the SN ratio to the biometric information processing server.

14. A biometric information detecting apparatus for transmitting a biometric state value measured by being attached to a physical body of a measured person to a biometric information processing server for carrying out a predetermined processing by way of a wireless, communication, the biometric information detecting apparatus comprising:
   a biometric sensor for measuring biometric information for a predetermined time period;
   amplifying means having a variable amplification factor for amplifying to output an output of the biometric sensor;
   amplification factor setting means for setting the amplification factor of the amplifying means;
   A/D conversion means for acquiring the sampling data by subjecting the output of the biometric sensor to A/D conversion;
   storing means for storing the sampling data;
   frequency analyzing means for subjecting the sampling data stored to the storing means to a frequency analysis and storing a result of the frequency analysis to the storing means;
   biometric state value calculating means for calculating the biometric state value from the result of the frequency analysis stored to the storing means;
   average amplification factor calculating means for calculating an average amplification factor of the amplification factor set by the amplification factor setting means within the predetermined time period; and
   communicating means for transmitting the biometric state value and the average amplification factor to the biometric information processing server.

15. A biometric information detecting apparatus for transmitting a biometric state value measured by being attached to a physical body a measured person to the biometric information processing server for carrying out a predetermined processing by way for a wireless communication, the biometric information detecting apparatus comprising:
   a biometric sensor for measuring biometric information for a predetermine time period;
   a mounting sensor for detecting whether the biometric sensor is correctly mounted;
   A/D conversion means for acquiring a sampling data by subjecting an output of the biometric sensor to A/D conversion;
   storing means for storing the sampling data;
   frequency analyzing means for subjecting the sampling data stored to the storing means to a frequency analysis and storing a result of the frequency analysis to the storing means;
   biometric state value calculating means for calculating the biometric state value from the result of the frequency analysis stored to the storing means;
   mounting rate calculating means for calculating a mounting rate of the biometric sensor within the predetermined time period based on an output of the mounting sensor; and
   communicating means for transmitting the biometric state value and the mounting rate of the biometric sensor to the biometric information processing server.

16. A biometric information processing server for receiving via wireless communication a biometric state value measured by attaching a biometric information detecting apparatus to a physical body of a measured person and carrying out a predetermined processing, the biometric information processing server comprising:
   communicating means for receiving the biometric state value and an SN ratio from the biometric information detecting apparatus;
   determining means for determining a reliability of the biometric state value based on whether the SN ratio exceeds a predetermined threshold; and
   measured data storing means for associating a result of the reliability determination with the biometric state value and storing the result of the reliability determination and the biometric state value.

17. A biometric information detecting method comprising:
   providing a biometric information detecting apparatus comprising a biometric sensor for measuring biometric information for a predetermined time period, A/D conversion means for acquiring a sampling data by subjecting an output of the biometric sensor to A/D conversion, storing means for storing the sampling data, and measured data storing means for storing a data of a measurement result;
   a frequency analyzing procedure for subjecting the sampling data stored to the storing means to a frequency analysis and storing a result of the frequency analysis to the storing means;
   a biometric state value calculating procedure for calculating a biometric state value from the result of the frequency analysis stored to the storing means;
   an SN ratio calculating procedure for calculating an SN ratio from the result of the frequency analysis stored to the storing means;
   a determining procedure of determining a reliability of the biometric state value based on whether the SN ratio exceeds a predetermined threshold; and
   a measured data storing procedure for associating a result of determining the reliability determination with the biometric state value and storing the result of the reliability determination and the biometric state value to the measured data storing means.

18. A biometric information detecting method comprising:
   providing a biometric information detecting system comprising: (a) a biometric information detecting apparatus comprised of a biometric sensor for measuring biometric information for a predetermined time period, A/D conversion means for acquiring a sampling data by subjecting an output of the biometric sensor to A/D conversion, storing means for storing the sampling data, biometric state value calculating means for calculating a biometric state value by the biometric information detecting apparatus being attached to a physical body of a measured person, SN ratio calculating means for calculating an SN ratio, and communicating means for transmitting the calculated biometric state value and SN ratio; and (b) a biometric information processing server comprised of communicating means for receiving the biometric state value and the SN ratio from the biometric information detecting apparatus, and measured data storing means for storing a data of a measurement result;

a frequency analyzing procedure of subjecting the sampling data stored to the storing means to a frequency analysis and storing a result of the frequency analysis to the storing means;

a biometric state value calculating procedure of calculating the biometric state value by the biometric state value calculating means from the result of the frequency analysis stored to the storing means;

an SN ratio calculating procedure of calculating the SN ratio by the SN ratio calculating means from the result of the frequency analysis stored to the storing means;

a determining procedure of determining a reliability of the biometric state value based on whether the SN ratio exceeds a predetermined threshold; and a measured data storing procedure by the measured data storing means of associating a result of the reliability determination with the biometric state value and storing the result of the reliability determination and the biometric state value to the measured data storing means.

19. A biometric information apparatus according to claim 1; further comprising communicating means for communicating information via wireless communication; means for measuring the biometric state value based on a measurement schedule received from a server by way of the communicating means; and means for transmitting the result of the reliability determination and the biometric state value to the server.

20. A biometric information detecting apparatus according to claim 1; wherein the biometric information is an artery wave and the biometric state value is a pulse number.

\* \* \* \* \*